United States Patent [19]

Tully et al.

[11] Patent Number: 4,801,700

[45] Date of Patent: * Jan. 31, 1989

[54] PROCESS FOR THE PREPARATION OF 1,6-DICHLORO-1,6-DIDEOXY-β-D-FRUCTOFURANOSYL-4-CHLORO-4-DEOXY-α-GALACTOPYRANOSIDE

[75] Inventors: William Tully, Swords; Nicholas M. Vernon, Dublin; Peter A. Walsh, Blackrock, all of Ireland

[73] Assignee: McNeilab, Inc., Spring House, Pa.

[*] Notice: The portion of the term of this patent subsequent to Nov. 8, 2005 has been disclaimed.

[21] Appl. No.: 921,285

[22] Filed: Oct. 20, 1986

[30] Foreign Application Priority Data

Oct. 21, 1985 [GB] United Kingdom ............... 8525953

[51] Int. Cl.$^4$ .................. C07H 1/00; C07H 5/02; C07H 15/24
[52] U.S. Cl. .................... 536/125; 536/18.4; 536/18.5; 536/124; 536/122
[58] Field of Search ............... 536/18.4, 18.5, 124, 536/125, 122

[56] References Cited

U.S. PATENT DOCUMENTS

| | | | |
|---|---|---|---|
| 4,002,609 | 1/1977 | Khan | 536/119 |
| 4,343,934 | 8/1982 | Jenner et al. | 536/122 |
| 4,362,869 | 12/1982 | Jenner et al. | 536/125 |
| 4,380,476 | 4/1983 | Mufti et al. | 536/119 |
| 4,549,013 | 10/1985 | Hough et al. | 536/122 |
| 4,692,514 | 9/1987 | Chang | 536/124 |

FOREIGN PATENT DOCUMENTS

45-19488 of 1970 Japan .................. 536/125

*Primary Examiner*—Ronald W. Griffin
*Assistant Examiner*—Nancy S. Carson
*Attorney, Agent, or Firm*—Steven P. Berman

[57] ABSTRACT

A process for the preparation of 1,6-dichloro-1,6-dideoxy-β-D-fructofuranosyl-4-chloro-4-deoxy-α-galactopyranoside comprising the steps of (a) reacting sucrose with a tritylating agent; (b) acetylating the tritylated reaction product; (c) detritylating the acetylated reaction product; (d) isomerizing the resulting pentaacetate; (e) chlorinating the isomerized product; and (f) deacetylating the chlorinated reaction product.

5 Claims, No Drawings

4,801,700

PROCESS FOR THE PREPARATION OF 1,6-DICHLORO-1,6-DIDEOXY-$\beta$-D-FRUCTOFURANOSYL-4-CHLORO-4-DEOXY-$\alpha$-GALACTOPYRANOSIDE

BACKGROUND OF THE INVENTION

This invention relates to a process for the preparation of 1,6-dichloro-1,6-dideoxy-$\beta$-D-fructofuranosyl-4-chloro-4-deoxy-$\alpha$-galactopyranoside. This compound is a potent sweetener, having a sweetness several hundred times that of sucrose. Its use as a sweetener and in sweetening compositions is disclosed in U.S. Pat. No. 4,435,440.

The preparation of 1,6-dichloro-1,6-dideoxy-$\beta$-D-fructofuranosyl-4-chloro-4-deoxy-$\alpha$-galactopyranoside or as it is sometimes referred to in the literature, 4,1',6'-trichloro-4,1',6'-trideoxygalactosucrose, (hereinafter referred to as "sucralose") involves the substitution of chlorine atoms in the sucrose molecule in one of the five secondary hydroxyl positions and in two of the three primary hydroxyl positions. This particular selection of positions usually means that any synthetic route must involve the preparation of an intermediate sucrose derivative having the required positions available for chlorination while the other positions are blocked. In particular, the reactive 6-position must not be chlorinated, while the 4-position must be rendered available for chlorination.

One route proposed in the literature (Fairclough et al, Carbohydrate Research 40 (1975) 285-298) involves the formation of the 6,1',6'-tritrityl derivative of sucrose, peracetylation of the molecule and then detritylation with migration of the 4-acetyl radical to the 6-position, to give 2,3,6,3',4'-penta-O-acetylsucrose which has the correct hydroxy groups unprotected. Subsequent reaction with a chlorinating agent provides the 4,1',6'-trichlorogalactosucrose penta-acetate which in turn yields sucralose on removal of the acetyl groups. The chlorination proceeds with inversion of configuration at the 4-position. The 1' and 6'-positions freely rotate, but the 4-position cannot and the glucose ring is thus inverted at the 4-position yielding a galactose derivative so that the product is a galactosucrose.

Another route is set forth in U.S. Pat. No. 4,380,476 and comprises the steps of: (a) reacting sucrose with an acylating reagent under conditions to provide a mixture of acylated sucrose derivatives containing a major proportion of 6-monoacylated material; (b) optionally separating the 6-monoacylated sucrose derivative from other acylated derivatives before step (c); (c) reacting the monoacylated sucrose derivative with a chlorinating reagent capable of chlorinating at positions 1', 4 and 6' of a sucrose 6-acylate; and (d) deacylating and separating (in either order) the sucralose material formed.

A further process for preparing sucralose is set forth in U.S. Pat. No. 4,362,869. This process converts sucrose through a number of steps into sucralose. This process describes the sequential steps of (1) tritylation of sucrose to block the three primary alcohol groups; (2) acetylation of the five secondary alcohol groups as acetates; (3) detritylation of the three primary alcohol groups to deblock them; (4) acetyl migration from the 4-position to the 6-position; (5) chlorinating the desired alcohol groups at positions 4, 1', 6'; and (6) deblocking the remaining five alcohol groups by deacetylation thereby yielding sucralose.

The invention disclosed in U.S. Pat. No. 4,362,869 is centered around the acetyl migration from the 4-position to the 6-position which is effected by treating a solution of 2,3,4,3',4'-penta-O-acetyl sucrose in an inert solvent with a weak acid at an elevated temperature. It was found that selection of specific reaction conditions for the acetyl migration gave considerably higher yields overall for separate detritylation and migration than the prior art which taught a one stage process for these steps. The weak acid utilized is preferably a carboxylic acid, especially an aliphatic carboxylic acid such as acetic acid. It is stated that any acid having an acid strength of the same order as acetic acid under the conditions used will suffice. The reaction temperature should be elevated above ambient temperature in order to provide an acceptable reaction time. A temperature of from about 80° to 150° C. is said to be suitable, preferably 100° to 130° C.

The inert solvent is said to be any solvent for penta-O-acetyl sucrose which remains liquid at the elevated temperature selected, e.g. a temperature in the range of 100° to 140° C. Ketonic solvents are particularly preferred, especially methyl isobutyl ketone, which refluxes at about 117° C. A dilute solution of the acid in the solvent is said to be suitable, e.g. a solution of from 2 to 10% by weight, especially about 5%. This degree of dilution is suitable for reaction with the sucrose penta-acetate dissolved at a concentration of up to 30% by weight, e.g. about 20%. Ester solvents of sufficiently high boiling point are also useful, e.g. n-butyl acetate. Also of particular interest are aromatic hydrocarbons such as toluene or xylene.

When the reaction is completed, the reaction mixture is cooled an 2,3,6,3',4'-penta-O-acetylsucrose crystallizes. After an additional period of time at 0° C., the crystalline product is filtered, washed and dried and then proceeds to the chlorination step. While an effective process, the above process involves the use of a carboxylic acid at high temperatures in the presence of free hydroxyl groups, conditions known to promote acylation.

The prior art also reveals that dilute aqueous solutions of bases are suitable for carrying out acetyl migrations. Although a migration occurs from the 4 to the 6 positions of the glucose ring with 0.001 N sodium hydroxide, the yield is very low due to concurrent deacetylation. When 2 to 5% solutions of a very weak base, pyridine or substituted pyridines, e.g. 2,4 and 2,6 lutidines or 2,4,6 tri-methyl pyridine (collidine) are used in water, reasonable yields of 2,3,6,3',4'-penta-O-acetyl sucrose are obtained, however, deacetylation and further migration to give 3,4,6,3',4'-penta-O-acetyl sucrose also occurs.

It is an object of the present invention to provide an improved process for the preparation of sucralose.

It is a further object of the present invention to provide a process for the preparation of sucralose wherein the acetyl migration step of U.S. Pat. No. 4,362,869 can be accomplished without utilizing a weak acid.

These and other objects of the present invention will become apparent to one skilled in the art from the detailed description given hereinafter.

SUMMARY OF THE INVENTION

The foregoing objects and other features and advantages of the present invention are achieved by an improved process for the preparation of sucralose. This process comprises the steps of (1) tritylation of sucrose to block the three primary alcohol groups; (2) acetylation of the five secondary alcohol groups as acetates; (3) detritylation of the three primary alcohol groups to deblock them; (4) acetyl migration; (5) selective chlorination; and (6) deacetylation to deblock the remaining alcohol groups to yield sucralose.

DETAILED DESCRIPTION OF THE INVENTION

It has now been found that the acetyl migration can be carried out utilizing a weak base catalyst in a non-aqueous solvent. These bases should be kinetically active but sterically hindered to inhibit deacetylation and minimize side reactions. Specific base catalysts which have been found useful for acetyl migrations include tert-butylamine, triethylamine, pyrrolidine, di-N-propylamine, di-isopropylamine, morpholine, n-butylamine, isopropylamine, piperidine, diethylamine and the like.

The reaction temperature should be from about 30° C. to 60° C., preferably about 50° C. If the temperature is raised above 60° C. then the risk of side reactions increases and if the temperature is kept below about 30° C., the reaction may proceed too slowly. The reaction proceeds to completion in from about 2½ hours to 10 hours depending on the selected amine and temperature.

The migration takes place in any inert solvent in which 2,3,4,3',4'-penta-O-acetyl sucrose is sparingly soluble, excluding alcohols or primary and secondary amines, where potential for a base catalyzed deacetylation reaction exists. The migration takes place in the following representative solvents: toluene, tetrahydrofuran, methylene chloride, ethyl acetate, acetone, acentonitrile, pyridine (with stronger base catalyst like tert-butylamine). The best solvents are those in which the product, being only partially soluble, crystallizes out early and drives the reaction to completion. Toluene, ethyl acetate and methyl isobutylketone are examples of this class. High amine concentrations inhibit crystallization and for this reason the catalyst level should not exceed about 8%.

A major embodiment of this invention is that the acetyl migration and chlorination reactions leading to sucralose can be carried out not only in discrete steps but also in tandem without the necessity of separating out the migrated product prior to chlorination provided are chosen:

(a) a solvent compatible to both reactions, and
(b) a base catalyst easily removed prior to chlorination.

The selected solvent should, in particular, be inert to the chlorinating agents and have a boiling point high enough to ensure complete chlorination, preferably above about 80° C.

The aromatic hydrocarbons such as toluene, xylene and the like are suitable, as are ethyl acetate, methyl isobutylketone, dichloroethane and other solvents which satisfy the earlier state requirements.

As discussed above, the first step of the process involves the tritylation of sucrose to block the three primary alcohol groups. This can be accomplished by reacting sucrose with trityl chloride in a suitable solvent such as pyridine. It has also been noted that increased yields at lower costs can be achieved when the solvent is changed from pyridine to dimethylformamide wherein a tertiary (e.g. N-methylmorpholine) or polymer-bound (e.g. poly-2 vinylpyridine) amine is used as acid scavenger.

After completion of the reaction and the blocking of the three primary alcohols, the tritylated reaction product is subjected to in-situ peracetylation with acetic anhydride. If pyridine is used as a solvent, the reaction mixture after acetylation is poured into ice water and the precipitated product filtered and dried. The procedure is repeated a number of times to remove any traces of pyridine and a crystallization yields 6,1',6'-tri-O-tritylsucrose penta-acetate.

If dimethylformamide is used as the solvent during tritylation, then the N-methylmorpholine hydrochloride can be neutralized in-situ by the addition of sodium hydrogen carbonate and the solution concentrated to remove N-methylmorpholine and a large portion of the dimethylformamide. Acetic anhydride and a catalyst such as pyridine, 4-dimethylaminopyridine or potassium acetate are added to the residue. After reaction, crystallization by methanol addition affords yields 6,1',6'-tri-O-tritylsucrose penta-acetate. Alternatively, the dimethylformamide and N-methylmorpholine are removed by extracting from toluene with water and the tritritylsucrose acetylated in toluene solution.

The detritylation step can be accomplished by dissolving the 6,1',6'-tri-O-tritylsucrose penta-acetate in dichloromethane and acetic acid, cooling the solution to 0° C. and adding concentrated hydrochloric acid. After stirring for two hours, the solution is neutralized. After additional stirring and concentration, methanol is added resulting in the precipitation of triphenylmethanol. The solution is then concentrated and ether is added and 2,3,4,3',-4'-penta-O-acetylsucrose is crystallized out at room temperature.

Other methods of detritylating the 6,1',6'-tri-O-tritylsucrose penta-acetate (TRISPA) can also be utilized. For example, hydrogen chloride can be reacted with the penta-acetate solution in toluene at about 0° C. with the 2,3,4,3',4'-penta-O-acetylsucrose isolated by filtration and the trityl chloride recovered by concentration of the mother liquid. The detritylation can also be accomplished in a methylene chloride solution using hydrogen chloride as the catalyst in methanol, in methylene chloride/formic acid solution by the dropwise addition of water, or in methylene chloride using a Lewis acid.

The 2,3,4,3',4'-penta-O-acetylsucrose is then subjected to the acetyl migration as discussed above followed by chlorination of the resulting 2,3,6,3',4'-penta-O-acetylsucrose. The chlorination can be accomplished utilizing any suitable chlorinating reagent. These reagents include Vilsmeier type reagents (e.g. dimethylformamide/thionyl chloride), triphenylphosphine/carbon tetrachloride in a suitable solvent such as methyl isobutylketone and sulphuryl chloride/pyridine; thionyl chloride/triphenylphosphine oxide or any other suitable chlorinating reagent.

The chlorination results in the formation of 4,1',6'-trichloro-4,1',6'-trideoxygalactosucrose pentaacetate. The deacetylation can be achieved with methanol and sodium methoxide to yield the desired sucralose.

Specific embodiments of the present invention are illustrated by the following representative examples. It will be understood, however, that the invention is not confined to the specific limitations set forth in the individual examples but rather to the scope of the appended claims.

EXAMPLE I

Tritylation and Acetylation

Sucrose (50 g, 0.14 mol) is mixed with N-methylmorpholine (60 g. 0.59 mol) in dimethylformamide (100 mls) at 50° C. trityl chloride (141.8 g of 97% purity, 0.49 mol) is added in three portions over 2.5 hours and heating continues for 3.5 hours. Sodium hydrogen carbonate (42.7 g, 0.5 mol) is added and heating at 50° C. continues for one hour. All solvents are removed under vacuum and the residue is dissolved in acetic anhydride (96.6 mls, 1.02 moles). Potassium acetate (15.6 g, 0.15 moles) is added and heating at 115° C. is undertaken for 3 hours. After cooling methanol (400 mls) is added and after crystallization is complete a solid (183.2 g) was obtained which contained 6,1,6'-tri-O-tritylsucrose penta-acetate (TRISPA) (124.6 g, 68.6% yield).

EXAMPLE II

Tritylation and Acetylation

Sucrose (40 g, 0.11 mol) is mixed with N-methylmorpholine (50 g, 0.49 mol) in dimethylformamide (120 mls) at 50° C. trityl chloride (95 g of 97% purity, 0.33 mol) dissolved in hot (60° C.) toluene (60 mls) is added in three portions over the same number of hours. Heating is continued for three further hours after which toluene (140 mls) is added. The mixture is extracted with 50 ml portions of brine at 60° C. (to prevent emulsions forming). On complete removal of the N-methylmorpholine hydrochloride and the dimethylformamide the toluene/tritrityl sucrose is dried by azeotroping off the water. Acetylation with acetic anhydride (75 mls, 0.8 mol) and pyridine (5 mls) at 90° C. for 3 hours is followed by cooling and crystallization with methanol (420 mls) yielding as solid (112.7 g). The TRISPA content was 91.4% (103 g) implying a 68.9% yield.

EXAMPLE III

Tritylation and Acetylation

To an agitated mixture at 40° C. of sucrose (50 g, 0.146 mol), dimethylformamide (100 ml) and dry activated poly-2-vinylpyridine (63 g, 0.53 mole equivalents) was added in three charges trityl chloride (3×44.7 g) at hourly intervals. The mixture, held at 40° C. for a further 12 hours, was filtered free of the polymer, washing the filter cake successively with hot methylene chloride and acetone. The combined filtrate and washings were evaporated to dryness under vacuum. To the viscous residue (206.7 g) was added acetic anhydride (116.5 g, 1.1 mol) and 4-dimethylaminopyridine (3 g) and the resultant solution was agitated at 80° C. for 2 hours. To the cooled mixture was added methanol (200 ml) and the TRISPA (117.8 g), slightly contaminated with tritanol, was filtered in a yield of 53.7%.

EXAMPLE IV

Detritylation

TRISPA (200 g) is dissolved in toluene (800 ml) and the solution is cooled to 0° C. Hydrogen chloride gas (17.1 g) is passed into the cooled stirred solution over 4.5 hours, after which the slurry of precipitated 2,3,4,3',4'-penta-O-acetylsucrose (4-PAS) is stirred for 15 mins. The system is purged with nitrogen under vacuum for 1 hour to remove residual hydrogen chloride. The resultant mixture is filtered and washed with toluene (65 mls), granulated and reslurried in toluene containing 1% triethylamine (120 mls) for 10 mins. The mixture is again filtered, washed with toluene (65 ml) and dried and yields 87 g (80%, corrected for assay) of 2,3,4,3',4-penta-O-acetylsucrose (4-PAS). The mother liquor is concentrated to dryness giving crude trityl chloride (135 g, 95%, corrected for assays).

EXAMPLE V

Detritylation

TRISPA (50 g) is dissolved in $CH_2Cl_2$ 150 mls. Methanol (15 ml, containing HCl (0.5M), 0.2 equivalents) is added and the solution is stirred at room temperature for 4.5 hours. The HCl is neutralized with tertiary butyl amine (1 ml). The $CH_2Cl_2$ and methanol are evaporated at room temperature under vacuum, leaving a solid. The solid is slurried in methanol (120 ml) for 30 minutes, water (6 ml) is added and stirring is continued for 10 minutes. The tritylmethylether is filtered (28.4 g) and washed with a solution of water (2 ml) in methanol (48 ml). The filtrate is reduced to an oil under reduced pressure and ethyl acetate (100 ml) is added to axeotrope off any residual water. The oil was dried overnight at 40° C. under vacuum. The resulting product weighed 26.4 g, yield 58.2% correcting for assays.

EXAMPLE VI

Detritylation

TRISPA (25 g) was dissolved in methylene chloride (87 ml) at room temperature and formic acid (87 ml, 95%) added. Water (11 ml) was added to the stirred solution over a 5 minute period. After stirring for a further 5 mins the reaction was quenched by addition of water (100 ml) and the triphenyl methanol was filtered and washed with water (100 ml) and the filtrate and wash were combined, neutralized to pH 6.5 by addition of solid sodium carbonate and extracted with methylene chloride (1×100 ml, 2×25 ml). Concentration of the extracts gave 4-PAS as an oil in 79% yield. The triphenyl methanol yield was 15.4 g, 100%.

EXAMPLE VII

Detritylation

TRISPA (25 g) was dissolved in methylene chloride (75 ml). Aluminium trichloride (110.5 g) was added. The solution became warm and was stirred for one hour. Water (90 ml) was added. The layers were separated leaving the aluminium trichloride in the aqueous layer. Water (100 ml) was added and the methylene chloride evaporated under reduced pressure at ambient. The precipitated tritanol was filtered and the water extracted with $CH_2Cl_2$. The $CH_2Cl_2$ was evaporated to give 2,3,4,3',4'-penta-O-acetylsucrose (Yield 6 g, 60%).

EXAMPLE VIII

Acetyl Migration and Chlorination

4-PAS (150 g,) is dissolved in methylisobutylketone (750 ml) and heated at 50° C. for 5 hours with tert-butylamine (22.5 ml). The solution is concentrated to 600 ml in vacuo at 60° C. and triphenyl phosphine (336.5 g) and carbon tetrachloride (69.3 ml) are added. On heating to 60° C. an exotherm occurs raising the temperature to 105° C. and water (38.5 ml) and sodium bicarbonate (25.7 g) are added. After cooling to 0° C. with agitation, the precipitated triphenylphosphine oxide is separated by filtration and washed with cold methyl isobutylketone (100 ml). The combined filtrate and washings are concentrated to dryness, the residue being dissolved in alcohol (500 ml) and cooled to 0° C. The crystallized 4,1',6'-trichloro-4,1',6'-trideoxygalactosucrose penta-acetate (TOSPA) was isolated by filtration and dried. (88.0 g 60%, correcting for assays).

EXAMPLE IX

Acetyl Migration and Chlorination

4-PAS (50 g) is dissolved in pyridine (300 ml) and heated at 50° C. for 4 hours with tert-butylamine (5 ml). 50 ml of pyridine is removed by vacuum distillation and the residue is cooled to −20° C. Sulphuryl chloride (25.5 ml) was added at a rate to keep the temperature below 10° C. Addition took 1 hour. The solution was rapidly heated to 100° C. for 1 min and then rapidly cooled. The pyridine was distilled off in vacuo at 50° C. to leave an oil (100 mls) which was poured into water with rapid stirring. The solid was collected by filtration and recrystallized from methanol to give TOSPA (23 g, 47% yield corrected for assays).

EXAMPLE X

Acetyl Migration

4-PAS (200 g) is mixed with ethylacetate (322 mls), heptane 28 mls) and tert-butylamine (21 mls) at 50° C. for 5 hours. 6-PAS is observed to crystallize during the reaction but complete crystallization is obtained by the addition of heptane (124 mls) at the reaction temperature followed by cooling and stirring for 3 hours. After filtration and washing of the cake with a mixture of ethylacetate-heptane (100 mls) it is dried in a vacuum oven at 40° C. for 16 hours. A white solid (140.3 g) containing 85.4% 6-PAS (119.8 g) is obtained. Yield 85.4%.

EXAMPLE XI

Chlorination

To a slurry of 2,3,6,3',4'-penta-O-acetyl sucrose (59 g, 90.4 mmol.) and triphenylphosphine oxide (125.8 g, 454 mmol.) in 1,2-dichloroethane was added thionyl chloride (32.8 ml, 452 mmol.) at ambient and the mixture heated to reflux for 3 hours. Sodium bicarbonate (20 g) in 220 ml of water were added slowly and the biphasic mixture agitate for 0.5 hour. The organic layer was separated, evaporated to dryness under vacuum and methyl isobutyl ketone (150 ml) added. On cooling at 0° C. for 1 hour, triphenylphosphine oxide (ca. 98 g) separated and was isolated by filtration, washing the filter cake with methyl isobutyl ketone (50 ml). The mother liquor was evaporated to dryness under reduced pressure and the residue recrystallized from ethanol, giving 4,1',6'-trichloro-4,1',6'-trideoxy-2,3,6,3',4'-penta-O-acetyl-galactosucrose (97.1 g), slightly contaminated with triphenylphosphine oxide.

EXAMPLE XII

Chlorination

To a slurry of 6-PAS (50 g) and triphenylphosphine sulphide (53.3 g) in xylene (150 ml) was added thionyl chloride (32.8 ml) and the mixture was heated at 115° C. for 4.5 hr. Water (300 ml) was added and the biphasic mixture was vigorously stirred at 0° C. for 1 hr. The crude TOSPA was isolated by filtration and recrystallization from hot methanol (Yield 31.8 g, 66% corrected for assays).

EXAMPLE XIII

De-Acetylation

TOSPA (50 g) is stirred at ambient with sodium methoxide (0.5 g) in methanol (125 ml) for 1.5 hours under vacuum. Heat is applied to maintain a temperature of 18°–20° C. TOSPA dissolves within 10 mins. The solution is neutralized by stirring with Amberlite IRC 50 (H+) resin (7.5 g) to, pH 7–7.5. The resin is removed by filtration and washed with methanol (25 ml), the filtrate and wash then being stirred with decolorizing charcoal (4 g) for 15 mins. The solution is clarified by filtrate and concentrated to a residue in vacuo. The sucralose is crystallized from ethyl acetate (100 ml), filtered, washed with ethyl acetate (25 mls) and dried in vacuo at 40° C. for 12 hours. Yield 26 g, 92% correcting for assays.

What is claimed is:

1. In a process for the preparation of 1,6-dichloro-1,6-dideoxy-β-D-fructofuranosyl-4-chloro-4-deoxy-α-galactopyranoside comprising the steps of:
    (a) reacting sucrose with a tritylating agent;
    (b) acetylating the tritylated reaction product with an acetylating agent to obtain 6,1',6'-tri-O-tritylsucrose penta-acetate;
    (c) detritylating the 6,1',6'-tri-O-tritylsucrose penta-acetate to obtain 2,3,4,3',4'-penta-O-acetylsucrose;
    (d) isomerizing the 2,3,4,3',4'-penta-O-acetylsucrose to obtain 2,3,6,3',4'-penta-O-acetylsucrose;
    (e) chlorinating 2,3,6,3',4'-penta-O-acetylsucrose to obtain 4,1',6'-trichloro-4,1',6'-trideoxygalactosucrose pentaacetate; and
    (f) deacetylating the chlorinated product; the improvement comprising effecting the isomeriation step in a non-aqueous solvent with a weak base at a temperature of from about 30° C. to 60° C.

2. A process according to claim 1 wherein the weak base is selected from the group consisting of tert-butylamine, triethylamine, pyrrolidine, di-N-propylamine, di-isopropylamine, morpholine, n-butylamine, isopropylamine, piperidine and diethylamine.

3. A process according to claim 2 wherein the weak base is tert-butylamine.

4. A process according to claim 1 wherein the isomerization step is carried out at a temperature of about 50° C.

5. A process according to claim 1, further improved by effecting the isomerization step (d) and chlorination step (e) without the necessity to separate the 2,3,6,3',4'-penta-O-acetylsucrose before chlorination.

* * * * *